United States Patent [19]
Shubkin

[11] 3,960,962
[45] June 1, 1976

[54] PROCESS FOR REPLACING THE HYDROXY GROUP OF AN AROMATIC HYDROXY COMPOUND WITH AN AMINE GROUP

[75] Inventor: Ronald L. Shubkin, West Bloomfield, Mich.

[73] Assignee: Ethyl Corporation, Richmond, Va.

[22] Filed: May 31, 1974

[21] Appl. No.: 474,944

[52] U.S. Cl.................................. 260/581; 252/430
[51] Int. Cl.$^2$......................................... C07C 85/06
[58] Field of Search......................... 260/563 D, 581

[56] References Cited
FOREIGN PATENTS OR APPLICATIONS
607,987    1/1935    Germany ............................. 260/581

OTHER PUBLICATIONS
Bruner et al., Inorg. Chem., 12(7), 1465–1470, (1973).

Grubbs et al., J. Am. Chem. Soc. 93, 3062–3063, (1971).

Primary Examiner—D. Horwitz
Attorney, Agent, or Firm—Donald L. Johnson; Robert A. Linn; Joseph D. Odenweller

[57] ABSTRACT

Aromatic hydroxy compounds (e.g., 2,6-dimethylphenol) are converted to the corresponding aromatic amine (e.g., 2,6-dimethylaniline) by reaction with ammonia at elevated temperatures in the presence of a cyclohexanone promoter and a catalyst comprising metallic palladium bonded to a phosphinated polystyrene resin.

2 Claims, No Drawings

PROCESS FOR REPLACING THE HYDROXY GROUP OF AN AROMATIC HYDROXY COMPOUND WITH AN AMINE GROUP

BACKGROUND

Resin-bound catalysts are known. Grubbs et al, J. Am. Chem. Soc. 93, 3062 (1971) and J. Am. Chem. Soc. 95, 2373 (1973), describe rhodium (I) bonded to a diphenyl phosphonium-substituted polystyrene resin. It functions as a hydrogenation catalyst. Pittman et al, Chem. Tech., 560, September 1973, describe a number of metal-containing catalysts (Cr, Mo, Fe, Mn, Ni, Co and Ti) bonded to such resins which have hydroformylation activity.

Haag et al, German OLS 1,800,380; 1,800,371 and 1,800,377 describe a number of resin-bound metallic catalysts, especially where the catalytic metal is bonded to an amine type anion exchange resin.

Bruner et al, Inorg. Chem. 12, No. 7, p. 1465, July 1973, describe a hydrogenation catalyst which consists of divalent palladium bonded to a diphenylphosphinomethylsubstituted polystyrene resin. None of these references disclose metallic palladium (zero valent) bonded to a phosphinated polystyrene resin nor the use of any of the catalysts in the amination of phenols.

SUMMARY OF THE INVENTION

According to the present invention a catalyst is provided which is zero valent palladium metal bonded to a phosphinated polystyrene resin. The catalyst is effective in catalyzing the reaction of ammonia with aromatic hydroxy compounds in the presence of a cyclohexanone to produce the corresponding aromatic amine. The catalyst retains good activity and is readily recovered for recycle.

DESCRIPTION OF THE PREFERRED EMBODIMENTS

A preferred embodiment of the invention is an improvement in a process for replacing the hydroxy group of an aromatic hydroxy compound with an -NH$_2$ group by reacting the aromatic hydroxy compound with ammonia in the presence of a cyclohexanone promoter and a catalyst. According to the improvement, the catalyst is metallic palladium bonded to a phosphinated polystyrene resin. Such catalyst retains activity through many cycles without special re-activation procedures. Other catalysts such as charcoal-supported palladium have greatly reduced activity on recycle and require a re-activation procedure prior to re-use.

The basic amination process is described in French 72/04144, in which the preferred catalyst is charcoal-supported palladium. The basic process is applicable to a broad range of hydroxy aromatics since the only reaction site involves the hydroxyl group bonded to a benzene ring. The rest of the hydroxy aromatic can be anything as long as it does not contain other substituents which would interfere with the course of the reaction, for example, by reacting with the aminating agent. The aryl portion of the molecule may be a mono-, di- or tri-nuclear radical, or for that matter, can contain even more aryl groups. The aryl portion of the hydroxy aromatic may also be fused to other cyclic systems including heterocyclic systems, such as those containing cyclo oxygen, nitrogen and sulfur rings. For example, the hydroxy aromatic can be any of the isomeric hydroxysubstituted derivatives of benzene, naphthalene, anthracene, phenanthrene, indene, isoindene, benzofuran, isobenzofuran, thionaphthene, indole, isoindole, indolenine, 2-isobenzazole, 1,2-benzodiazole, 1,3-benzodiazole, indiazine, 1,3-benzoisodiazole, 1,2,3-benzotriazole, benzisoxazole, benzoxadiazole, 1,2-benzopyran, 1,4-benzopyran, 1,2-benzopyrone, quinoline, isoquinoline, 1,3-benzodiazine, 1,2-benzisoxazine, acenaphthene, fluorene, dibenzopyrrole, xanthene, thianthrene, phenothiazine, phenoxazine, naphthacene, chrysene, pyrene, triphenylene, and the like, wherein the hydroxyl group is bonded to a nuclear carbon atom.

The process is also applicable to aryl hydroxy compounds having more than one hydroxyl radical bonded to a nuclear aromatic carbon atom. For example, the process can be applied to such polyhydroxy aromatics as hydroquinones, resorcinols, catechols, 1,3-dihydroxy naphthalenes, pyrogallols, phloroglucinols, and the like.

Substituents other than hydroxyl groups may be present in the aromatic compounds as long as they do not interfere with the course of the reaction. That is to say, the other substituents should be relatively inert to ammonia and hydrogen and should not act to poison the catalyst. For example, any of the previously-listed aromatics may be substituted in a variety of positions with alkyl radicals, aralkyl radicals, cycloalkyl radicals, chlorine, bromine, iodine, fluorine, and the like. A few representative examples of these using the simpler aromatic structure are p-chlorophenol, β-bromo-α-naphthol, β-chloro-7-hydroxy-coumarone, 2-acetoxy-7-hydroxy-indolenine, 3-n-dodecyl-7-hydroxy-benzisoxazole, 8-hydroxy-1,2-benzopyran, 7-sec-octadecyl-8-hydroxy-isocoumarin, and the like.

The reaction proceeds very well when the hydroxy aromatic is a hydroxy-substituted benzene. As previously, these phenol type materials can be substituted with other groups as long as they do not interfere with the course of the reaction. A preferred class of such hydroxy-substituted benzenes are those having the formula:

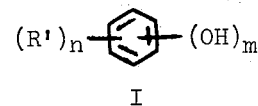

I wherein n is an integer from 0-3, m is an integer from 1-3, and R is selected from the group consisting of aliphatic alkyl radicals containing from 1-50 carbon atoms, aralkyl radicals containing from 7-20 carbon atoms and cycloalkyl radicals, containing from 6-20 carbon atoms. Some examples of these are: phenol, catechol, resorcinol, pyrogallol, phlurorglucinol, hydroquinone, 3,5-di-tert-butylphenol, 2,6-di-tert-butylhydroquinone, 3-methylcatechol, p-cresol, m-cresol, p-pentacontyl phenol, 2,4-didodecyl phenol, p-cyclohexyl phenol, 3-cyclooctyl phenol, p-(4-sec-dodecylcyclohexyl)phenol, 2,4,6-tri-methyl phluoroglucinol, m-sec-eicosyl phenol, p-(4-tert-tridecylbenzyl)phenol, 4-(3,5-di-sec-heptylcyclohexyl)phenol, and 2-sec-pentacontyl hydroquinone.

The advantages of the process are greater when the hydroxy-substituted benzene is a mononuclear phenol in which at least one position ortho to the phenoxide oxygen atom is substituted with a radical selected from the group consisting of primary and secondary alkyl radicals containing from 1-50 carbon atoms, mononuclear aryl radicals containing from 6-20 carbon atoms, cycloalkyl radicals containing from 6-20 carbon atoms and primary and secondary aralkyl radicals containing from 7-20 carbon atoms. These are phenols having the formula:

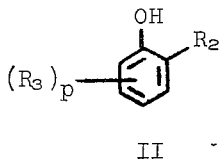

II wherein p is an integer from 0-2, $R_2$ is selected from the group consisting of primary and secondary aliphatic alkyl radicals containing from 1-50 carbon atoms, primary and secondary aralkyl radicals containing from 7-20 carbon atoms, mononuclear aryl radicals containing from 6-20 carbon atoms and cycloalkyl radicals containing from 6-20 carbon atoms, and $R_3$ is selected from the group consisting of aliphatic alkyl radicals containing from 1-50 carbon atoms, aralkyl radicals containing from 7-20 carbon atoms, mononuclear aryl radicals containing from 6-20 carbon atoms, and cycloalkyl radicals containing from 6-20 carbon atoms. Some examples of these phenolic starting materials are:
o-sec-butylphenol,
2,5-dimethylphenol,
o-cresol,
o-ethylphenol,
2,4,6-tri-sec-butylphenol,
2,4-dimethylphenol,
4-($\alpha,\alpha$-dimethylbenzyl)-o-cresol,
2-($\alpha$-methylbenzyl)phenol,
2-cyclohexyl-p-cresol,
2-cyclooctyl-p-cresol,
2-(3,5-di-tert-butyl-cyclohexyl)-4-sec-eicosylphenol,
2-sec-pentacontylphenol,
2-($\alpha$-methyl-4-dodecylbenzyl)phenol,
2-phenylphenol,
2-(4-tetradecylphenyl)phenol,
2-(3,5-di-sec-heptylphenyl)phenol,
2-triacontylphenol,
2-isopropylphenol,
2,4-di-sec-dodecylphenol, and
2-($\alpha$-methyl-4-sec-amylbenzyl)phenol.

An especially valuable feature of the basic process is its ability to replace an aromatic hydroxyl radical with an amine radical when both positions on the aromatic nucleus ortho to the hydroxyl group are substituted. When the aromatic hydroxy compound is a mononuclear phenol the phenolic reactant has the formula:

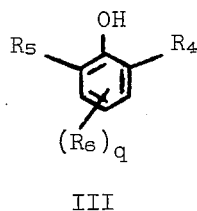

III wherein q is 0 or 1, and $R_4$ and $R_5$ are selected from the same group as $R_2$ in Formula II, and $R_6$ is selected from the same group as $R_3$ in Formula II. Some examples of these phenols are:

2-methyl-6-tert-butylphenol,
2,6-dimethylphenol,
2,4,6-trimethylphenol,
2,6-di-sec-butylphenol,
2,6-di-sec-butyl-p-cresol,
2,6-di-tert-butylphenol,
2,4-dimethyl-6-sec-butylphenol,
2,6-diisopropylphenol,
2,6-di-sec-octylphenol,
2,6-di($\alpha$-methylbenzyl)phenol,
6-($\alpha$-methylbenzyl)-o-cresol,
2,4-di-methyl-6-(2,3-benzobenzyl)phenol,
2-(3-tert-butyl-5-isopropylbenzyl)phenol,
2-cyclooctyl-6-ethylphenol,
2,6-dibornylphenol,
2,6-dicyclohexylphenol,
6-sec-pentacontyl-o-cresol,
2,4-dimethyl-6-docosylphenol,
6-phenyl-o-cresol,
2,4-dimethyl-6-(4-tetradecylphenyl)phenol,
2-ethyl-6-(3,5-diheptylphenyl)-p-cresol, and the like.

The amount of ammonia added is not critical. On a mole basis it may be less than the hydroxy aromatic or it may be an excess of the hydroxy aromatic. This does not affect the operability of the process but only the optimization of yield. In general, it is preferred to use a molar excess of ammonia. A useful range based on hydroxy aromatic is from about 0.5-50 moles of ammonia per mole of hydroxy aromatic. A preferred range is from 1-10 moles of ammonia per mole of hydroxy aromatic.

It is essential that the reaction mixture contain a promoter amount of a cyclohexanone. Without this there is substantially no reaction under the reaction conditions. Although extremely small amounts will cause the reaction to proceed, it has been found that, in general, the reaction proceeds at a satisfactory rate when the mixture contains at least about 0.05 mole of a cyclohexanone per mole of hydroxy aromatic. There is no critical upper limit, but for economic reasons, a most useful range is from about 0.1 to about 0.5 mole of cyclohexanone per mole of hydroxy aromatic.

The cyclohexanone used as the catalyst can be any compound containing a six-membered cycloaliphatic ketone in its structure. The cyclohexanone catalyst can correspond in structure with the cyclohexanone which would form by partial reduction of the hydroxy aromatic compound or it can be an entirely different cyclohexanone. Although not bound by any theory as to how the process operates, it is believed that the cyclohexanone promoter functions by forming an imine derivative with the aminating agent which then transfers hydrogen to the hydroxy aromatic, forming an aromatic amine and regenerating cyclohexanone catalyst, thus making the reaction self-propagating. Hence, no matter what cyclohexanone compound is added initially to start the reaction, the cyclohexanone present after the reaction is under way will correspond in structure to that of the partially reduced hydroxy aromatic compound. This series of reactions can be illustrated by the following equations in which phenol represents the hydroxy aromatic.

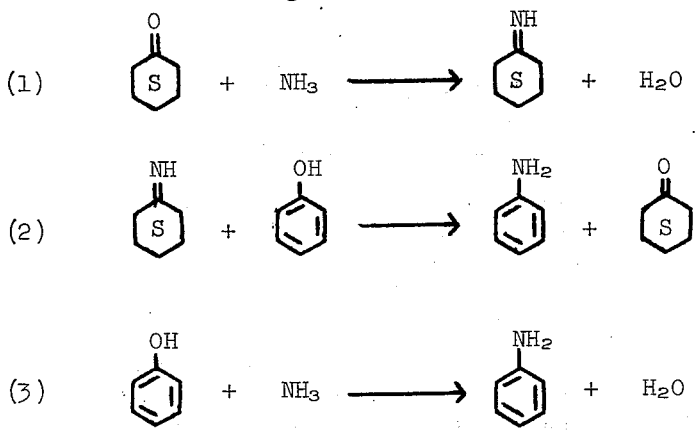

The result of the above is that the cyclohexanone consumed in reaction (1) is regenerated by reaction (2), and the cyclohexylimine formed in reaction (1) is consumed in reaction (2). The net result is represented by reaction (3): the hydroxy aromatic group attached to the aromatic group is replaced with an amine group. Whatever the mechanism, the results are that only a catalytic amount of the cyclohexanone is required to initiate the reaction and the hydroxy aromatic is aminated by the ammonia.

As stated above, any cyclohexanone can be used to initiate the reaction. Cyclohexanones corresponding in structure to the partially reduced hydroxy aromatic are preferred. For example, the cyclohexanone of partially reduced phenol is the compound cyclohexanone. Likewise, the partially reduced alkylated hydroxybenzenes are the alkylated cyclohexanones. The following examples serve to illustrate that is meant by the cyclohexanone corresponding in structure to the partially reduced hydroxy aromatics.

| Hydroxy Aromatic | Cyclohexanone Corresponding in Structure to Partially Reduced Hydroxy Aromatics |
|---|---|
| 2,6-dimethylphenol | 2,6-dimethylcyclohexanone |
| o-cresol | 2-methylcyclohexanone |
| 2,6-diisopropylphenol | 2,6-diisopropylcyclohexanone |
| 2,4-dimethylphenol | 2,4-dimethylcyclohexanone |
| 2,4,6-trimethylphenol | 2,4,6-trimethylcyclohexanone |
| 2,6-diisopropylphenol | 2,6-diisopropylcyclohexanone |
| 2,6-di-sec-butylphenol | 2,6-di-sec-butylcyclohexanone |
| o-sec-butylphenol | 2-sec-butylcyclohexanone |
| α-naphthol | 2,3-benzocyclohexanone |

The cyclohexanone promoter need not be added as such at the start of the process but can be formed in situ by adding a small amount of a reducing agent. Thus, the process can be conducted by reacting a hydroxy-substituted aromatic with ammonia in the presence of a promoter amount of a cyclohexanone formed in situ by adding an amount of a reducing agent sufficient to reduce a portion of said hydroxy-substituted aromatic to said catalytic amount of a cyclohexanone, in contact with a catalyst at a temperature of from about 200°-400°C.

The reducing agent employed can be any of those known to be capable of reducing a hydroxy aromatic to the corresponding cyclohexanone. One such group of useful reducing agents is the hydroaromatics. These are compounds containing a 6-membered cycloaliphatic structure which can lose hydrogen and form an aromatic compound (Fieser and Fieser, Advanced Organic Chem., p. 645, Reinhold Publishing Co., N.Y. 1961). Some typical examples of these are: decalin, tetralin, cyclohexane, cyclohexanol, and the like. Other organic reducing agents such as hydroquinone, catechol, and the like, can also be used. Compounds that form hydrogen in contact with water are also useful. These include sodium aluminum hydride, sodium borohydride, calcium hydride, lithium aluminum hydride, and the like.

The most preferred reducing agent is hydrogen. Thus, the reaction can be initiated by adding hydrogen to the reaction mixture in an amount sufficient to reduce some of the hydroxy aromatic to form a promoter amount of the cyclohexanone as previously described. Once the cyclohexanone promoter has formed no additional reducing agent is required. The amount of hydrogen added should be at least enough to form 0.05 mole of a cyclohexanone per mole of hydroxy aromatic. An excess is generally employed because it does not all react. The formation of the cyclohexanone promoter can be readily accomplished by adding the hydroxy aromatic and catalyst to a reaction vessel and then pressurizing the vessel with about 10–1000 psig, preferably 400–600 psig, of hydrogen and heating the mixture to about 100°C until sufficient hydrogen has been reacted to form the promoter. This is about 5–50 mole per cent of the hydroxyaromatic. Following this, ammonia can be added and the process completed. Use of aqueous ammonia is preferred. Of course, if desired, water and ammonia can be added prior to the reduction. A very facile method of carrying out the process is to place the hydroxy aromatic and catalyst in the reaction vessel and then pressurize the vessel with a mixture of hydrogen and ammonia while stirring at reaction temperature.

Although a solvent is not required in the process, the use of a solvent is not detrimental. Preferred solvents are liquid hydrocarbons boiling in the range of from about 50°-200°C. Useful examples include hexane, heptane, octane, nonane, decane, benzene, toluene, xylene, and the like.

The reaction proceeds at elevated temperatures of from about 175°-500°C. A preferred operating temperature is from about 200°-400°C.

The process can be carried out as a batch or continuous operation. In a batch operation the hydroxy aromatic, cyclohexanone promoter, ammonia and catalyst can be merely mixed together and heated in a sealed vessel to reaction temperature. Amination is usually complete in 1–12 hours. Preferred reaction time is 1–8 hours. Optionally, the hydroxy aromatic, cyclohexanone promoter and catalyst can be mixed in a closed vessel, heated to reaction temperature, and then ammonia added over an extended period of time. In still another mode of operation the hydroxy aromatic and catalyst can be placed in a reaction vessel together with a small amount of a reducing agent such as tetralin. This mixture is then heated, causing the formation of a promoter amount of the cyclohexanone corresponding in structure to the hydroxy aromatic, following which the ammonia is added and the reaction completed at elevated temperature.

In another variation of this in situ promoter formation method the hydroxy aromatic and catalyst are placed in a sealed reaction vessel which is then pressurized with from about 10–100 psig with hydrogen and heated until a promoter amount of a cyclohexanone forms. Following this, ammonia is added and the reacton completed.

A simple method of carrying out the process is to merely place the hydroxy aromatic, catalyst, ammonia and hydrogen in a pressure reaction vessel and heat to reaction temperature while stirring. Water is also included in order to prevent deactivation of the catalyst for hydrogenation of the hydroxy aromatic by ammonia.

In the continuous method the hydroxy aromatic, cyclohexanone and ammonia are passed through a fixed bed catalyst maintained at reaction temperature at a space velocity such that the residence time is sufficient to provide a good conversion to aromatic amine. In one version of the continuous process a mixture of hydroxy aromatic, ammonia, water and hydrogen is passed through the fixed bed catalyst which causes the cyclohexanone to form in situ, which in turn promotes the amination reaction on the aromatic hydroxy compound.

The catalyst according to the present improved process is zero valent or metallic palladium bonded to a phosphinated polystyrene resin. The resin may be cross-linked to improve physical properties by cross-linking agents such as divinyl benzene. Such resins include dihydrocarbyl benzylphosphine units in the polymer chain, such as

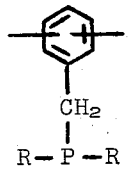

wherein R is an alkyl, cycloalkyl, aralkyl, alkaryl or aryl. Representative alkyl groups are methyl, ethyl, butyl, dodecyl, and the like. Representative cycloalkyl groups are cyclohexyl, 4-methylcyclohexyl, cyclooctyl, and the like. Representative aralkyl groups are benzyl, 4-methylbenzyl, 4-tert-butylbenzyl, and the like. Representative alkaryl groups are 4-methylphenyl, 2,4-diethylphenyl, 4-tert-octylphenyl, 4-sec-dodecylphenyl, and the like. Representative aryl groups are phenyl, naphthyl, and the like. Preferably, R is a phenyl group such that the substituent on the styrene polymer is a diphenylphosphinomethyl group.

The phosphinated resins are readily prepared by the method described by Grubbs et al, J. Am. Chem. Soc. 93, 3062 (1971). This involves the reaction of lithium dihydrocarbylphosphine with a chloromethylated polystyrene resin. Chloromethylation is described by Pepper et al, J. Chem. Soc., (1953) p. 4097.

The phosphinated resin is reacted with a palladium salt or complex palladium salt, such as $PdCl_2$, $K_2PdCl_4$, $(NH_4)_2PdCl_4$, $Na_2PdCl_4$, and the like. The palladium compound is dissolved in a suitable solvent such as water, acetone, alcohol, dimethyl sulfoxide, dimethyl formamide, and the like. The phosphinated resin is added to the palladium solution. The mixture is stirred for a period sufficient to allow the palladium to react with the phosphine groups. A period of 30 minutes to several days can be used. Temperatures from room temperature to reflux are useful. The amount of palladium bound to the resin by this reaction depends upon the number of phosphinated sites available, assuming that sufficient palladium is in the solution to satisfy all available phosphine sites. Generally the degree of phosphination is such that the palladized resin contains about 0.1–15 weight per cent palladium. The palladium cation is chemically bound to the phosphine groups on the resin and is thus anchored in place.

Following this, the palladium cation is reduced to a zero valent or metallic state by treatment with a reducing agent such as hydrazine. This is readily accomplished by removing the resin-containing palladium cations from the palladium solution, drying it, and adding it to an aqueous hydrazine solution. Reduction is quite rapid, as shown by darkening of the resin, and is usually complete in about 15 minutes to 4 hours at temperatures from room temperature to reflux.

The following example illustrates the preparation of a catalyst for use in the improved amination process.

EXAMPLE 1

In a stirred reaction vessel was placed 104 grams of commercial polystyrene resin, 600 ml carbon disulfide and 80 grams of monochlorodimethyl ether (caution - carcinogen). The temperature was lowered to 5°C with an ice bath and 78.1 grams of stannic chloride added in small portions over a one hour period. The temperature was then allowed to rise slowly to 25°C and the mixture stirred overnight. The mixture was then cooled in an ice bath and 200 ml of water added. It was then filtered to recover the sand-like chloromethylated resin which was washed with water and acetone. The resin contained 15.04 per cent chlorine.

In a stirred reaction vessel was placed 250 ml of tetrahydrofuran. The vessel was flushed with nitrogen and 6.94 grams of lithium wire added. While stirring at 25°C, a solution of 110.3 grams of diphenylphosphine chloride in 250 ml of tetrahydrofuran was added over a one hour period. Stirring was continued at 25°C. After 22 hours all the lithium had not been consumed, so an additional 11 grams of diphenylphosphine chloride was added and stirring continued for 2 hours. Then a slurry of 120 grams of the chloromethylated polystyrene prepared above in 500 ml of tetrahydrofuran was added to the lithium diphenylphosphine solution. The temperature rose slowly to 35°C and was cooled to 25°C. The red mixture turned orange in about 15 minutes and was stirred overnight. The mixture was light yellow at this time and was hydrolyzed with 500 ml of saturated aqueous ammonium chloride solution. The phosphinated resin was recovered by filtration and washed with water, tetrahydrofuran and benzene. Analysis showed it to contain 5.08 percent residual chlorine and 5.73 percent phosphorus.

In a stirred vessel was placed 100 ml of acetone, 3.1 grams of $PdCl_2$ and 10 grams of the above phosphinated polystyrene resin. The mixture was refluxed under nitrogen for 3 days. The palladized resin was recovered by filtration, washed with acetone, and dried under vacuum to give 12.7 grams of brown powder. The palladium bound to the resin was then reduced to zero valent state by adding the resin to 100 ml of 20 percent hydrazine hydrate in water at 55°C. The mixture immediately turned black and was stirred for 30 minutes. The metallic palladium resin-bound catalyst was recovered by filtration and washed with water and methanol and then dried under vacuum. Analysis showed it to contain 11.6 weight per cent palladium.

Other dihydrocarbyl phosphine chlorides could be substituted in the above reaction to obtain the corresponding phosphinated resins. Useful phosphinating materials include dimethylphosphine chloride, dibenzylphosphine chloride, diethylphosphine chloride, dibutylphosphine chloride, dicyclohexylphosphine chloride, di(4-methylphenyl)phosphine chloride, and the like.

The following example illustrates the use of the above catalyst in the amination of an aromatic hydroxy compound.

EXAMPLE 2

In a high pressure autoclave was placed 70.2 grams of 2,6-dimethylphenol, 67.5 grams of concentrated aqueous ammonia and 10 grams of the catalyst from Example 1. The autoclave was flushed with nitrogen, sealed and pressurized to 400 psig with hydrogen. While stirring, it was heated to 250°C and held at that temperature for 6 hours. Gas chromatographic analysis of the reaction mixture at that time based upon area percent was 62.36 per cent 2,6-dimethylaniline, 26.6 percent 2,6-dimethylphenol, 11.02 per cent reduced products (mainly 2,6-dimethylhexanone, 2,6-dimethylcyclohexanol and 2,6-dimethylcyclohexylimine). Recovery of 2,6-dimethylaniline product is readily accomplished by filtration to recover catalyst followed by distillation to recover product.

The recovered catalyst was recycled to a subsequent run and remained effective, although the reaction rate was lower.

The product anilines are useful as dye intermediates and antiknock agents for gasoline. The 2,6-di-lower alkyl anilines such as 2,6-dimethylaniline produced by the process are especially useful in making selective herbicides, as described in U.S. Pat. No. 3,544,305; 3,547,620; 3,557,210 and 3,655,755.

I claim:

1. In a process for replacing the hydroxy group of an aromatic hydroxy compound with a -$NH_2$ group, said process comprising reacting said aromatic hydroxy compound with ammonia in the presence of a cyclohexanone promoter and a catalyst at a temperature of about 200°–400°C, the improvement wherein said catalyst is palladium, said palladium being reduced by hydrazine to a metallic state and being bonded to a phosphinated polystyrene resin, said resin being characterized by having the group -$CH_2$-$P(R)_2$ bonded to phenyl groups in said polystyrene resin wherein R is selected from the group consisting of alkyl, cycloalkyl, aralkyl, alkaryl and aryl.

2. The improved process of claim 1 wherein R is phenyl.

* * * * *